(12) United States Patent
Chen et al.

(10) Patent No.: US 10,138,239 B2
(45) Date of Patent: Nov. 27, 2018

(54) PREPARATION METHOD OF CRYSTALLINE FORM A OF PCI-32765

(71) Applicant: CRYSTAL PHARMATECH CO., LTD., Suzhou, Jiangsu (CN)

(72) Inventors: Minhua Chen, Jiangsu (CN); Yanfeng Zhang, Jiangsu (CN); Liang Zhang, Shanghai (CN); Shulin Ji, Jiangsu (CN)

(73) Assignee: Crystal Pharmatech Co. LTD, Suzhou (CN)

( * ) Notice: Subject to any disclaimer, the term of this patent is extended or adjusted under 35 U.S.C. 154(b) by 0 days.

(21) Appl. No.: 15/559,777

(22) PCT Filed: Mar. 18, 2016

(86) PCT No.: PCT/CN2016/076779
§ 371 (c)(1),
(2) Date: Sep. 19, 2017

(87) PCT Pub. No.: WO2016/150349
PCT Pub. Date: Sep. 29, 2016

(65) Prior Publication Data
US 2018/0065958 A1    Mar. 8, 2018

(30) Foreign Application Priority Data

Mar. 20, 2015 (CN) .......................... 2015 1 0126412

(51) Int. Cl.
| | | |
|---|---|---|
| *C07D 471/04* | (2006.01) | |
| *C07D 487/04* | (2006.01) | |
| *C07D 211/32* | (2006.01) | |
| *G01N 23/20* | (2018.01) | |
| *G01N 25/48* | (2006.01) | |

(52) U.S. Cl.
CPC .......... *C07D 471/04* (2013.01); *C07D 211/32* (2013.01); *C07D 487/04* (2013.01); *G01N 23/20075* (2013.01); *G01N 25/4866* (2013.01)

(58) Field of Classification Search
CPC .. C07D 471/04; C07D 211/32; C07D 487/04; G01N 23/20075; G01N 25/4866
See application file for complete search history.

(56) References Cited

U.S. PATENT DOCUMENTS

2015/0158871 A1* 6/2015 Purro .................. C07D 487/04
514/262.1

FOREIGN PATENT DOCUMENTS

| CN | 103121999 A | 5/2013 | |
|---|---|---|---|
| WO | WO-2013184572 A1 * | 12/2013 | ........... C07D 487/04 |
| WO | 2015081180 A1 | 6/2015 | |
| WO | WO-2015081180 A1 * | 6/2015 | ........... C07D 487/04 |

OTHER PUBLICATIONS

McLoughlin, C. M., "Microwave-vacuum drying of pharmaceutical powders." Drying Technology 21.9 (2003): 1719-1733.*
Lee, A. Y., "Crystal polymorphism in chemical process development." Annual review of chemical and biomolecular engineering 2 (2011): 259-280.*
Tiwari, R., "Solid dispersions: an overview to modify bioavailability of poorly water soluble drugs." International Journal of PharmTech Research 1.4 (2009): 1338-1349.*
Marriam-Webster Dictionary https://www.merriam-webster.com/dictionary/tilde; 2018; p. 1-9.*

* cited by examiner

*Primary Examiner* — John M Mauro
(74) *Attorney, Agent, or Firm* — VLP Law Group LLP; Kent H. Cheng

(57) ABSTRACT

A preparation method of PCI-32765 crystalline form A, which comprises the following steps: 1) dissolving free base of PCI-32765 in a good solvent; 2) the solution prepared by Step 1) is dropwise added into an anti-solvent, stirred and added seed crystal of PCI-32765 Form A; Or the solution prepared by Step 1) is dropwise added into the suspension containing seed crystal of PCI-32765 Form A; 3) solution obtained by step 2) is continuously stirred and aged until crystal transformation is completed, then the crystal slurry is obtained; 4) crystal slurry in step 3) is filtered, washed, and dried to obtain the powder of PCI-32765 Form A. The preparation method of crystalline Form A provided by the present disclosure is a simple process and can be easily controlled, scaled up stably and conducted reliably. The process has high yield, good impurity removing capacity and is environmentally friendly. In addition, Form A provided by the present disclosure can be stably stored, and the hygroscopicity and solubility of Form A meet the requirements for medicinal use.

17 Claims, 2 Drawing Sheets

PREPARATION METHOD OF CRYSTALLINE FORM A OF PCI-32765

FIELD

The present disclosure relates to the field of pharmaceutical chemistry, particularly relates to preparation method of crystalline Form A of PCI-32765.

BACKGROUND

PCI-32765 (Formula I) is developed by American biopharmaceuticals company Pharmacyclics. It was approved by the U.S. Food and Drug Administration (FDA) on Nov. 13, 2013 as a single therapy for mantle cell lymphoma. PCI-32765 is also called Ibrutinib. Ibrutinib, as a targeted agent, can be selectively inhibiting Bruton's tyrosine kinase (BTK), which is an important medium of at least three key B-cell survival mechanisms. BTK's multiple mode of action can enable a B-cell malignant tumor into lymph tissue, so that the tumor cells can survive by getting necessary microenvironment. US Food and Drug Administration (FDA) has granted the compound (Ibrutinib) breakthrough status for the treatment of two kinds of B-cell malignancies.

The chemical name of the compound is 1-[(3R)-3-[4-amino-3-(4-phenoxyphenyl)-1H-pyrazolo[3,4-D]pyrimidin-1-yl]-1-piperidinyl]-2-propen-1-one, the structure is shown as below:

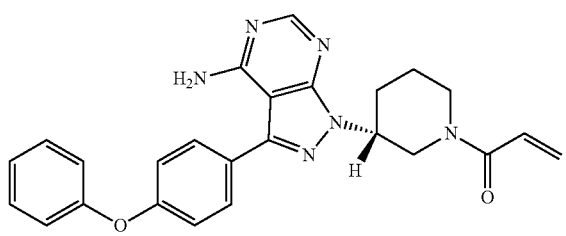

(I)

CN104327085A discloses a novel pharmaceutically available crystalline form of PCI-32765, named as Form A, which has an X-ray powder diffraction pattern comprising the following 2 theta values measured using CuKa radiation: 5.2°±0.2°, 17.6°±0.2°, 22.1°±0.2°, 19.3°±0.2°, 22.4°±0.2°, 20.8°±0.2°, and it also discloses the preparation method of Form A. This preparation method of Form A in prior art can be only used in lab test. So far, no stable and reliable preparation method for producing large scale of Form A has been disclosed.

In order to solve the problems in the prior art, it is necessary to provide preparation method of PCI-32765 Form A which is suitable for industrial large-scale production.

SUMMARY

The present disclosure aims to provide a preparation method of PCI-32765 crystalline Form A. Compared with the prior art, the preparation method disclosed by present disclosure can be easily controlled, scaled up stably and reliably and is suitable for industrial large-scale production.

To solve the above technical problem, the present disclosure uses the following technical solution:

The preparation method of PCI-32765 crystalline Form A wherein the preparation method comprises the following steps:

1) Preparing a PCI-32765 free base solution by dissolving the free base solid of PCI-32765 in a good solvent;

2) Adding dropwise the solution prepared by Step 1) into an anti-solvent, then stirring at a temperature of 0~20° C. and adding seed crystals of PCI-32765 Form A; Or adding dropwise the solution prepared by Step 1) into a suspension containing seed crystals of PCI-32765 Form A at a temperature of 0~20° C.;

3) Continuously stirring the solution obtained by step 2) and aging the solution until crystal transformation is completed, then a crystal slurry is obtained;

4) Filtering the crystal slurry in step 3) to obtain a filter cake, then washing and drying the filter cake to obtain a powder of PCI-32765 Form A.

The term "good solvent" can be a single or a mixed solvent. In present disclosure, it refers to a single or a mixed solvent in which PCI-32765 free base has good solubility.

Preferably, the good solvent is methanol or a mixed solvent containing methanol.

According to the present disclosure, the mixed solvent is methanol and dimethyl sulfoxide with a volume ratio of 1:0.8~1.2.

Preferably, the PCI-32765 free base solution in step 1) was prepared at a temperature of 10~50° C.

The term "anti-solvent" has ordinary meaning in this field. In present disclosure, it refers to the solvent in which Form A will precipitate when it is added.

Preferably, the anti-solvent is pure water.

Preferably, the mass ratio of the seed crystals of PCI-32765 crystalline Form A in step 2) and PCI-32765 free base in step 1) is 0.01~0.1:1.

Preferably, in step 1), the good solvent to PCI-32765 free base volume/weight ratio (mL/g) is 10~40:1.

Preferably, the anti-solvent in step 2) to PCI-32765 free base in step 1) volume/weight ratio (mL/g) is 30~80:1.

Preferably, in step 2), the solution in step 1) is dropwise added into the anti-solvent or suspension at a rate of 1~30 mL/min.

Preferably, the temperature in step 2) is 0~10° C.

More preferably, the temperature in step 2) is 0~5° C.

Preferably, the temperature for aging in step 3) is 0~40° C.

More preferably, the temperature for aging in step 3) is 0~30° C.

More preferably, the temperature for aging in step 3) is 0~20° C.

Preferably, the time for aging in step 3) is 5~48 hours.

More preferably, the time for aging in step 3) is 5~24 hours.

More preferably, the time for aging in step 3) is 14~20 hours.

According to the present disclosure, the step 3) comprises continuously stirring the solution obtained in step 2) and then aging at a constant temperature of 0~5° C. for 15~24 hours; Or maintaining the solution obtained in step 2) at a temperature of 0~5° C. for 1~3 hours and then heating to 10~20° C., and maintaining at a temperature of 10~20° C. for 10~15 hours to obtain the crystal slurry.

Preferably, the filter cake in step 4) is washed with pure water.

Preferably, the drying in step 4) comprises: placing the washed sample in a vacuum oven at 30~50° C. and drying the washed sample to a constant weight.

The advantages of the disclosure are shown as following:

The preparation method of crystalline Form A provided by the present disclosure has simple operating process and its procedure is stable and controllable. The process has high yield, good impurity removing capacity, and is environmentally friendly. In addition, Form A provided by the present disclosure can be stably stored, and the hygroscopicity and solubility of Form A meet the requirements for medicinal use.

The preparation method in this disclosure breaks through the bottlenecks of prior art which is difficult to produce Form A on a large scale, solving the problem of industrial large-scale production of Form A.

DETAILED DESCRIPTION

Figure 1:
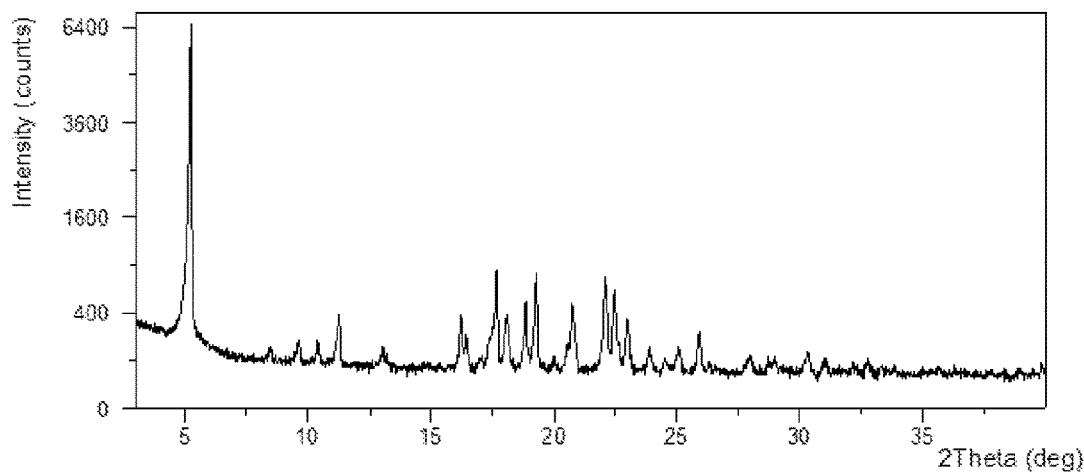
FIG. 1 shows the X-ray powder diffraction pattern of PCI-32765 crystalline Form A.

The inventor studied and optimized the process, and discovered a preparation method of the crystal Form A which can be used for industrial large-scale production. The preparation method in this disclosure breaks through the bottlenecks of prior art which is difficult to produce Form A on a large scale, solving the problem of industrial large-scale production of Form A.

The preparation method of crystalline Form A provided by the present disclosure has simple process and can be easily controlled, scaled up stably and reliably. The process has high yield, good impurity removing capacity and is environmentally friendly. In addition, Form A provided by the present disclosure can be stably stored, and the hygroscopicity and solubility of Form A meet the requirements for medicinal use.

The present disclosure will be further explained by the specific examples, but is not intended to limit the scope of the present disclosure. The skilled in the art can make improvements to the process and the used instruments within the scope of the claims, and those improvements should be considered as falling into the scope of the present disclosure. Accordingly, the protective scope of the present disclosure patent should be defined by the appended claims.

Crude PCI-32765 free base was commercially purchased as the starting material in the present disclosure. Preparation examples was conducted under regular conditions or the conditions suggested by the manufacturer. The room temperature generally refers to 25° C. without particularly specified The abbreviations in present disclosure are explained as follows:

XRPD: X-ray Powder Diffraction
DSC: Differential Scanning calorimetry
TGA: Thermal Gravimetric Analysis X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree The pattern of differential scanning calorimetry (DSC) in the present disclosure was acquired by a TA Q2000. The parameters of the differential scanning calorimetry (DSC) method of the present disclosure were as follow:

Heating rate: 10° C./min
Purge gas: nitrogen.

The pattern of thermal gravimetric analysis (TGA) in the present disclosure was acquired by a TA Q5000. The parameters of the thermal gravimetric analysis (TGA) method of the present disclosure were as follow:

Heating rate: 10° C./min;
Purge gas: nitrogen.

EXAMPLE 1

The preparation of PCI-32765 crystalline Form A: three batches of PCI-32765 crystalline Form A were produced according to the following method.

1) 35.0 g of PCI-32765 free base was charged, and then 1260 mL of methanol was added at room temperature. After pre-filtration, the clear solution was stored at 25~40° C. for using.

2) 1000 mL of pure water was added into a 10 L jacketed crystallizer, then stirring and cooling procedures were opened, the temperature of the system was controlled at about 0° C. 3.5 g seed crystals of PCI-32765 crystalline Form A was added into the crystallizer. Subsequently, pure water was further added into the crystallizer until system volume was 2520 mL. The suspension containing the seed crystals of crystalline Form A was stirred and obtained.

3) The solution of PCI-32765 freebase in step 1) was dropwise added into the suspension in step 2) at a constant rate for about 1 hour. After the adding was finished, it was maintained at the temperature of 0° C. for 2 hours. And then the crystallization system was heated up to 20° C. within 4 hours. The crystal slurry was obtained after aging for 14 hours. The crystalline form of the product was tested by XRPD. And it was transformed into crystalline Form A completely.

4) Wet filter cake was obtained by filtering the crystal slurry in step 3). And wet filter cake was washed with 70 mL of pure water and then dried in a vacuum oven at 45° C. for about 20 hours until constant weight.

The scale of the first batch prepared above was 35 g. The weight of the solid product was 35.4 g, the yield was 91.1% and the purity was 100.0%. The product was tested by XRPD. It was identified as PCI-32765 crystalline Form A.

The method of the second batch was the same as the first. The scale is 50 g, the weight of the solid product was 50.75 g, the yield was 91.5% and the purity was 99.8%. The product was tested by XRPD. It was identified as PCI-32765 crystalline Form A.

The method of the third batch was the same as the first. The scale is 75 g, the weight of the solid product was 75.2 g, the yield was 90.3% and the purity was 99.7%. The product was tested by XRPD. It was identified as PCI-32765 crystalline Form A.

Figure 2:
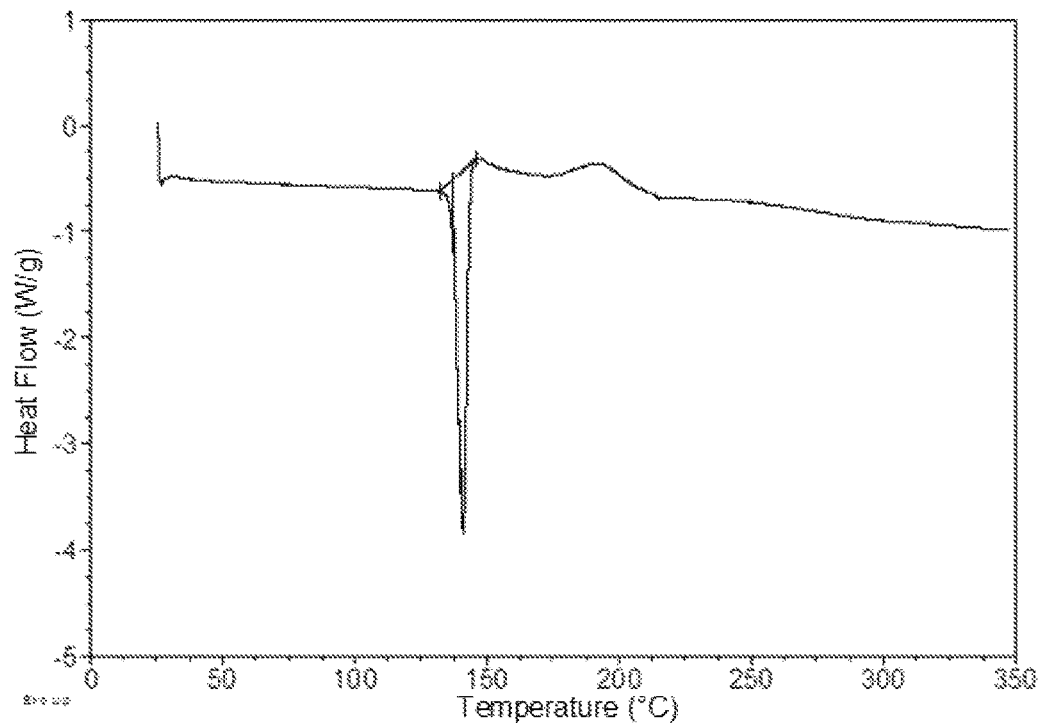
FIG. 2 shows the differential scanning calorimetry thermogram of PCI-32765 Form A.
Figure 3:
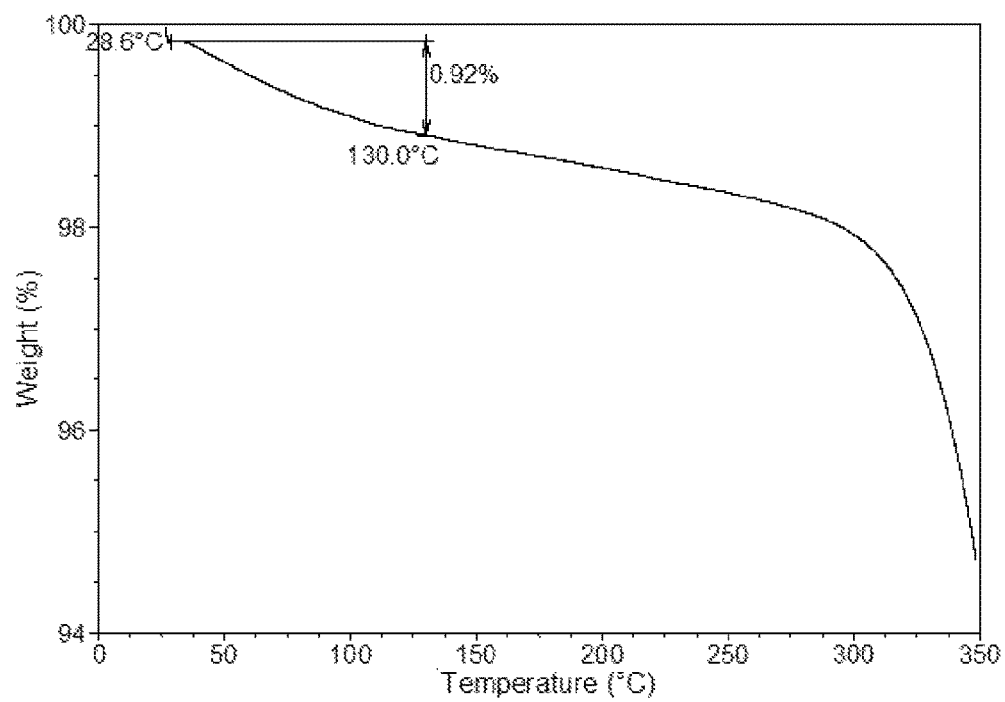
FIG. 3 shows the thermal gravimetric analysis thermogram of PCI-32765 crystalline Form A.

The X-ray powder diffraction data of crystalline form produced in this example was listed in Table 1. The XRPD pattern was displayed in FIG. 1, the DSC thermogram is displayed in FIG. 2 and the TGA thermogram is displayed in FIG. 3.

TABLE 1

| 2 theta | d-spacing | intensity % |
|---------|-----------|-------------|
| 5.23    | 16.91     | 100.00      |
| 11.26   | 7.86      | 4.69        |
| 16.22   | 5.47      | 4.86        |
| 16.44   | 5.39      | 2.12        |
| 17.65   | 5.03      | 12.28       |
| 18.09   | 4.91      | 4.76        |
| 18.86   | 4.71      | 7.03        |
| 19.28   | 4.60      | 11.48       |
| 20.75   | 4.28      | 6.76        |
| 22.07   | 4.03      | 11.15       |
| 22.46   | 3.96      | 8.33        |
| 23.00   | 3.87      | 4.29        |
| 25.90   | 3.44      | 3.16        |

EXAMPLE 2

The preparation of PCI-32765 crystalline Form A: three batches of PCI-32765 crystalline Form A were produced according to the following method.

1) 50.1 g of PCI-32765 freebase solid was charged, then 1800 mL of methanol was added at room temperature. After pre-filtration, the clear solution was stored at 25~40° C. for using.

2) 1000 mL of pure water was added into a 10 L jacketed crystallizer, then stirring and cooling procedures were opened, the temperature of the system was controlled at about 0° C. 5.0 g seed crystals of PCI-32765 crystalline Form A was added into the crystallizer. Subsequently, pure water was also added into the crystallizer until system volume was 2600 mL. The suspension which contained the seed crystals of crystalline Form A was stirred and obtained.

3) The solution of PCI-32765 freebase in step 1) was dropwise added into the suspension in step 2) at a constant rate for about 1 hour. After the adding was finished, it was maintained at the temperature of 0° C. for 20 hours to obtain crystal slurry. The crystalline form of the product was tested by XRPD. And it was transformed into crystalline Form A completely.

4) Wet filter cake was obtained by filtering the crystal slurry of step 3). And wet filter cake was washed with 100 mL of pure water and then dried in a vacuum oven at 45° C. for about 20 hours until constant weight.

The scale of the first batch prepared above was 50 g. The weight of the solid product was 48.4 g, the yield was 86.8% and the purity was 99.9%. The product was tested by XRPD. It was identified as PCI-32765 crystalline Form A.

The method of the second batch was the same as the first. The scale is 5 g, the weight of the solid product was 4.8 g, the yield was 86.0% and the purity was 100.0%. The product was tested by XRPD. It was identified as PCI-32765 crystalline Form A.

The method of the third batch was the same as the first. The scale is 5 g, the weight of the solid product was 4.4 g, the yield was 78.0% and the purity was 100.0%. The product was tested by XRPD. It was identified as PCI-32765 crystalline Form A.

The X-ray powder diffraction data of crystalline form produced in this example was listed in Table 2.

TABLE 2

| 2 theta | d-spacing | intensity % |
|---------|-----------|-------------|
| 5.18    | 17.06     | 19.84       |
| 11.25   | 7.87      | 12.41       |
| 16.19   | 5.47      | 35.00       |
| 16.43   | 5.40      | 16.26       |
| 17.34   | 5.11      | 16.63       |
| 17.63   | 5.03      | 19.00       |
| 18.06   | 4.91      | 30.56       |
| 18.85   | 4.71      | 28.54       |
| 19.28   | 4.60      | 62.29       |
| 20.73   | 4.28      | 26.85       |
| 22.06   | 4.03      | 100.00      |
| 22.43   | 3.96      | 21.09       |
| 22.99   | 3.87      | 40.74       |
| 23.87   | 3.73      | 11.47       |
| 25.89   | 3.44      | 11.11       |

EXAMPLE 3

The preparation of PCI-32765 crystalline Form A:

1) 10.0 g of PCI-32765 freebase solid was charge, then 160 mL of methanol at 50° C. was added. After pre-filtration, the clear solution was stored at 50° C. for using.

2) 0.99 g seed crystals of PCI-32765 crystalline Form A was added into 320 mL of pure water to make a suspension. The system temperature was controlled at about 2° C.

3) The solution of PCI-32765 freebase in step 1) was dropwise added into the suspension in step 2) at a constant speed for about 1 hour. After the adding was finished, it was maintained at the temperature of 2° C. for 1 hour. And then the crystallization system was heated up to 40° C. in 1 hour. The crystal slurry was obtained after aging for 16 hours. The crystalline form of the product was tested by XRPD. And it was transformed into crystalline Form A completely.

4) Wet filter cake was obtained by filtering the crystal slurry of step 3), and washed with 20 mL of pure water and then dried in a vacuum oven at 50° C. for about 20 hours until constant weight.

The weight of the solid product obtained by this batch was 10.1 g, the yield was 91.1% and the purity was 99.53%. Tested by XRPD, the product was identified as PCI-32765 crystalline Form A.

The X-ray powder diffraction data of crystalline form produced in this example was listed in Table 3.

TABLE 3

| 2 theta | d-spacing | intensity % |
|---------|-----------|-------------|
| 5.20    | 17.01     | 100.00      |
| 8.48    | 10.42     | 1.62        |
| 9.60    | 9.21      | 2.81        |
| 10.40   | 8.50      | 1.84        |
| 11.23   | 7.88      | 8.49        |
| 13.03   | 6.80      | 1.41        |
| 13.19   | 6.71      | 1.26        |
| 14.88   | 5.95      | 0.28        |
| 15.33   | 5.78      | 0.54        |
| 16.20   | 5.47      | 10.48       |
| 16.41   | 5.40      | 5.36        |
| 16.99   | 5.22      | 1.59        |
| 17.34   | 5.12      | 4.44        |
| 17.63   | 5.03      | 19.25       |
| 18.05   | 4.91      | 8.87        |
| 18.85   | 4.71      | 13.09       |
| 19.27   | 4.61      | 19.97       |
| 20.01   | 4.44      | 0.91        |
| 20.53   | 4.33      | 3.09        |
| 20.75   | 4.28      | 11.45       |
| 22.07   | 4.03      | 22.16       |

TABLE 3-continued

| 2 theta | d-spacing | intensity % |
|---|---|---|
| 22.45 | 3.96 | 13.29 |
| 22.98 | 3.87 | 9.27 |
| 23.88 | 3.73 | 2.60 |
| 24.52 | 3.63 | 1.47 |
| 25.04 | 3.56 | 2.74 |
| 25.89 | 3.44 | 5.38 |
| 26.32 | 3.39 | 1.07 |
| 26.57 | 3.35 | 0.76 |
| 27.77 | 3.21 | 1.15 |
| 27.95 | 3.19 | 1.99 |
| 28.72 | 3.11 | 1.44 |
| 28.94 | 3.09 | 1.82 |
| 29.51 | 3.03 | 0.35 |

EXAMPLE 4

The preparation of PCI-32765 Form A:

1) 9.99 g of PCI-32765 freebase solid was charged, then 160 mL of methanol was added at 50° C. After pre-filtration, the clear solution was stored at 50° C. for using.

2) 101.2 mg seed crystals of PCI-32765 Form A was charged, then 320 mL of pure water was added to obtain a suspension, and system temperature was controlled at about 5° C.

3) The solution of PCI-32765 freebase in step 1) was dropwise added to suspension of step 2) at a constant speed for about 1 hour. After addition was finished, it was maintained at 5° C. for 1 hour. Then the temperature of crystallization system was heated up to 40° C. within 1 hour and the crystal slurry was obtained. The crystalline form of the product was tested by XRPD. And it was transformed into crystalline Form A completely.

4) Wet filter cake was obtained by filtering the crystal slurry of step 3), and washed by 20 mL of pure water, then dried at 50° C. using a vacuum oven for about 20 hours until constant weight.

The weight of the solid product obtained by this batch was 9.5 g, the yield was 94.9% and the purity was 99.90%. Tested by XRPD, the product was identified as PCI-32765 crystalline Form A.

The X-ray powder diffraction data of crystalline form produced in this example was listed in Table 4.

TABLE 4

| 2 theta | d-spacing | intensity % |
|---|---|---|
| 5.20 | 17.00 | 16.22 |
| 8.48 | 10.43 | 5.70 |
| 9.57 | 9.24 | 10.69 |
| 11.21 | 7.89 | 23.34 |
| 13.16 | 6.73 | 2.80 |
| 16.17 | 5.48 | 41.85 |
| 16.43 | 5.39 | 20.04 |
| 16.98 | 5.22 | 6.93 |
| 17.35 | 5.11 | 19.37 |
| 17.59 | 5.04 | 33.02 |
| 18.05 | 4.92 | 40.14 |
| 18.83 | 4.71 | 40.51 |
| 19.24 | 4.61 | 76.19 |
| 20.77 | 4.28 | 35.60 |
| 22.05 | 4.03 | 100.00 |
| 22.42 | 3.97 | 26.77 |
| 22.96 | 3.87 | 46.03 |
| 23.86 | 3.73 | 12.36 |
| 24.50 | 3.63 | 3.71 |
| 25.01 | 3.56 | 12.77 |
| 25.87 | 3.44 | 14.74 |
| 26.37 | 3.38 | 2.68 |
| 27.85 | 3.20 | 6.13 |
| 28.90 | 3.09 | 9.63 |
| 29.42 | 3.04 | 1.71 |

EXAMPLE 5

The preparation of PCI-32765 Type A: two batches of PCI-32765 type A were produced according to following method.

1) 1.03 g of PCI-32765 freebase solid was charged, then 10 mL of methanol/dimethyl sulfoxide (v/v=1:1) was added at room temperature. After pre-filtration, the sealed solution was stored at 25~40° C. for using.

2) 100 mg of seed crystal of PCI-32765 Form A was charged, then 30 mL of pure water was added to prepare a suspension, and temperature of the system was controlled at about 0° C.

3) The solution of PCI-32765 freebase in step 1) was added into the suspension of step 2) at a constant rate for about 10 min. After the addition was finished, it was maintained at 0° C. for 20 hours to obtain the crystal slurry. The crystalline form of the product was tested by XRPD. And it was transformed into crystalline Form A completely.

4) Wet cake was obtained by filtering the crystal slurry of step 3), and washed by 2 mL of pure water, then dried at 45° C. using a vacuum oven for about 20 hours until the weight of the sample was constant.

The scale of above batch was 1 g, and the weight of obtained product was 0.89 g, the yield was 79.0% and the purity was 100%. Tested by XRPD, the product was identified as PCI-32765 crystalline Form A.

The method of second batch was same as the first, it was 0.3 g of scale, and the weight of obtained product was 0.27 g, the yield was 80.0% and the purity was 100.0%. Tested by XRPD, the product was identified as PCI-32765 crystalline Form A.

The X-ray powder diffraction data of crystalline form produced in this example was listed in Table 5.

TABLE 5

| 2 theta | d-spacing | intensity % |
|---|---|---|
| 5.20 | 17.00 | 36.43 |
| 11.22 | 7.89 | 12.08 |
| 16.19 | 5.48 | 33.84 |
| 16.41 | 5.40 | 23.53 |
| 17.37 | 5.11 | 19.71 |
| 17.63 | 5.03 | 22.57 |
| 18.08 | 4.91 | 33.43 |
| 18.87 | 4.70 | 30.72 |
| 19.29 | 4.60 | 63.34 |
| 20.84 | 4.26 | 25.71 |
| 22.08 | 4.03 | 100.00 |
| 22.45 | 3.96 | 23.36 |
| 23.03 | 3.86 | 41.70 |
| 23.90 | 3.72 | 11.90 |
| 25.12 | 3.54 | 10.19 |

CONTRASTIVE EXAMPLE 1

5.0 g of PCI-32765 freebase powder was charged, then 150 mL of isopropanol/n-heptane (v/v=2/3) was added, stirred at room temperature for 12 hours but failed to form clear solution.

CONTRASTIVE EXAMPLE 2

491 mg of PCI-32765 freebase powder was charged, then 16 mL isopropanol/n-heptane (v/v=1/5) was added, stirred at 50° C. for 12 hours but failed to form clear solution.

CONTRASTIVE EXAMPLE 3

102.4 mg of PCI-32765 freebase powder was charged, and it was dissolved in 4 mL of acetone at room temperature. After pre-filtration, 16 mL of n-heptane was added to the solution slowly, stirred overnight. The obtained product was tested by XRPD and confirmed to be Form A reported in WO2013184572A1.

Figure 4:
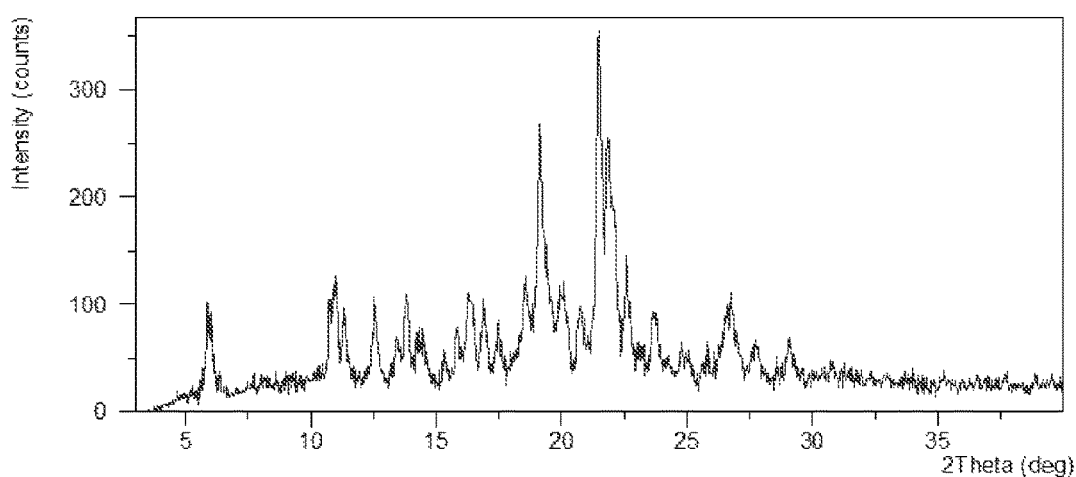
FIG. 4 shows the X-ray powder diffraction pattern of crystalline obtained in contrastive example 3.

The XRPD pattern of obtained product in this contrastive example is displayed in FIG. 4

The invention claimed is:

1. A preparation method of PCI-32765 crystalline Form A wherein the preparation method comprises the following steps:
   1) preparing a PCI-32765 free base solution by dissolving the free base solid of PCI-32765 in a solvent;
   2) adding dropwise the solution prepared by step 1) into an anti-solvent at a temperature of 0-20° C., then stirring the mixture at a temperature of 0-20° C. and adding seed crystals of PCI-32765 Form A to form a suspension; or adding dropwise the solution prepared by step 1) into a suspension containing seed crystals of PCI-32765 Form A at a temperature of 0-20° C. to form a suspensions;
   3) continuously stirring the suspension obtained by step 2) and aging the suspension until a crystal slurry is obtained;
   4) filtering the crystal in step 3) to obtain a filter cake, then washing and drying the filter cake to obtain a powder of PCI-32765 crystalline Form A.

2. The preparation method according to claim 1, wherein the solvent is methanol or a mixed solvent containing methanol.

3. The preparation method according to claim 2, wherein the mixed solvent is methanol and dimethyl sulfoxide with a volume ratio of 1:0.8-1.2.

4. The preparation method according to claim 1, wherein the PCI-32765 free base solution in step 1) is prepared at a temperature of 10-50° C.

5. The preparation method according to claim 1, wherein the anti-solvent is water.

6. The preparation method according to claim 1, wherein the mass ratio of the seed crystals of PCI-32765 crystalline Form A in step 2) and PCI-32765 free base in step 1) is 0.01-0.1:1.

7. The preparation method according to claim 1, wherein in step 1), the solvent to PCI-32765 free base volume/weight ratio (mL/g) is 10-40:1.

8. The preparation method according to claim 1, wherein the anti-solvent in step 2) to PCI-32765 free base in step 1) volume/weight ratio (mL/g) is 30-80:1.

9. The preparation method according to claim 1, wherein in step 2), the solution prepared by step 1) is dropwise added into the anti-solvent or suspension at a rate of 1-30 mL/min.

10. The preparation method according to claim 1, wherein the temperature in step 2) is 0-10° C.

11. The preparation method according to claim 10, wherein the temperature in step 2) is 0-5° C.

12. The preparation method according to claim 1, wherein the temperature for aging in step 3) is 0-40° C.

13. The preparation method according to claim 12, wherein the temperature for aging in step 3) is 0-30° C.

14. The preparation method according to claim 13, wherein the temperature for aging in step 3) is 0-20° C.

15. The preparation method according to claim 1, wherein the step 3) comprises continuously stirring the solution obtained by step 2) and then aging at a constant temperature of 0-5° C. for 15-24 hours; or maintaining the solution obtained by step 2) at a temperature of 0-5° C. for 1-3 hours and then heating to 10-20° C., and maintaining at a temperature of 10-20° C. for 10-15 hours to obtain the crystal slurry.

16. The preparation method according to claim 1, wherein the filter cake in step 4) is washed with water.

17. The preparation method according to claim 1, wherein the filter cake is dried in step 4) by placing the filter cake in a vacuum oven at 30-50° C. and drying to a constant weight.

* * * * *